(12) United States Patent
Kwon et al.

(10) Patent No.: US 10,946,003 B2
(45) Date of Patent: Mar. 16, 2021

(54) FORMULATION HAVING IMPROVED PH-DEPENDENT DRUG-RELEASE CHARACTERISTICS, CONTAINING ESOMEPRAZOLE OR PHARMACEUTICALLY ACCEPTABLE SALT THEREOF

(71) Applicant: HANMI PHARM. CO., LTD., Gyeonggi-do (KR)

(72) Inventors: Taek Kwan Kwon, Gyeonggi-do (KR); Kwang Young Lee, Gyeonggi-do (KR); Ho Taek Im, Gyeonggi-do (KR); Yong Il Kim, Gyeonggi-do (KR); Jae Hyun Park, Gyeonggi-do (KR); Jong Soo Woo, Gyeonggi-do (KR)

(73) Assignee: HANMI PHARM. CO., LTD., Gyeonggi-do (KR)

( * ) Notice: Subject to any disclaimer, the term of this patent is extended or adjusted under 35 U.S.C. 154(b) by 0 days.

(21) Appl. No.: 16/319,161

(22) PCT Filed: Jul. 24, 2017

(86) PCT No.: PCT/KR2017/007933
§ 371 (c)(1),
(2) Date: Jan. 18, 2019

(87) PCT Pub. No.: WO2018/021772
PCT Pub. Date: Feb. 1, 2018

(65) Prior Publication Data
US 2019/0240209 A1  Aug. 8, 2019

(30) Foreign Application Priority Data

Jul. 25, 2016 (KR) .................. 10-2016-0094238

(51) Int. Cl.
| | | |
|---|---|---|
| *A61K 31/4439* | (2006.01) | |
| *A61K 9/28* | (2006.01) | |
| *A61K 9/20* | (2006.01) | |
| *A61K 9/50* | (2006.01) | |
| *A61P 1/04* | (2006.01) | |
| *A61K 9/00* | (2006.01) | |

(52) U.S. Cl.
CPC ........ *A61K 31/4439* (2013.01); *A61K 9/0002* (2013.01); *A61K 9/20* (2013.01); *A61K 9/28* (2013.01); *A61K 9/2846* (2013.01); *A61K 9/2886* (2013.01); *A61K 9/50* (2013.01); *A61K 9/5026* (2013.01); *A61K 9/5073* (2013.01); *A61P 1/04* (2018.01); *A61K 9/2893* (2013.01)

(58) Field of Classification Search
None
See application file for complete search history.

(56) References Cited

U.S. PATENT DOCUMENTS

2007/0026071 A1    2/2007  Namburi et al.
2010/0272798 A1*  10/2010  Akiyama ............. A61K 9/5078
                                                                 424/461

FOREIGN PATENT DOCUMENTS

| JP | 2007524646 A | 8/2007 | | |
|---|---|---|---|---|
| KR | 1020100078462 A | 7/2010 | | |
| KR | 101084659 B1 | 11/2011 | | |
| KR | 1020120104991 A | 9/2012 | | |
| KR | 1020140076998 A | 6/2014 | | |
| KR | 102060738 B1 | 12/2019 | | |
| RU | 2412694 C2 | 9/2009 | | |
| WO | 2005009410 A2 | 2/2005 | | |
| WO | 2005051362 A2 | 6/2005 | | |
| WO | WO 2005/051362 | * | 6/2005 | ............... A61K 8/28 |
| WO | 2010026993 A1 | 3/2010 | | |

OTHER PUBLICATIONS

Malik, D., et al., "Formulation and evaluation of press coated tablets of esomeprazole for colonic delivery", "Asian Journal of Pharmaceutics", 2012, pp. 252-258, vol. 6, No. 4, Publisher: BRNSS Institutions.
Boehringer Ingelheim France, "Instructions for medical use of Dulcolax drug enteric coated tablets, 5 mg. manufactured by Boehringer ingelheim international GmbH, Registration No. P N015358/01 of Apr. 21, 2010 with changes of Jun. 6, 2012", Jun. 6, 2012.
Boehringer Ingelheim France, "Instructions for medical use of Dulcolax drug enteric coated tablets, 5 mg. manufactured by Boehringer ingelheim international GmbH, Registration No. P N015358/01 of Apr. 21, 2010 with changes of Jun. 6, 2012", Jun. 6, 2012, Page(s) Eng Trans.
"Instructions for medical use of a drug for medical use Esomeprazole Canon. Registration No. LP-003017", Jun. 2, 2015.
"Instructions for medical use of a drug for medical use Esomeprazole Canon", Jun. 2, 2015, Page(s) Eng Trans.
Bhatt, H., et al., "Solubility Enhancement of Budesonide and Statistical Optimization of Coating Variables for Targeted Drug Delivery", "Journal of Pharmaceutics", 2014, pp. 1-3, vol. 2014, No. article id: 262194, Publisher: Hindawwi Publishing Corporation.

(Continued)

*Primary Examiner* — Craig D Ricci
(74) *Attorney, Agent, or Firm* — Hultquist, PLLC; Steven J. Hultquist (57) ABSTRACT

Disclosed is a pharmaceutical formulation containing esomeprazole or a pharmaceutically acceptable salt thereof. The pharmaceutical formulation, based on considerably improved pH-dependent drug release characteristics, starts to release the esomeprazole or a pharmaceutically acceptable salt thereof at a target delay time after oral administration, continues the release for a predetermined time, and finishes the release after a predetermined time, thereby providing excellent patient convenience and excellent therapeutic effects, as compared to conventional other formulations.

6 Claims, 1 Drawing Sheet
(1 of 1 Drawing Sheet(s) Filed in Color)

(56) References Cited

OTHER PUBLICATIONS

Cheng, G., et al., "Time- and pH-dependent colon-specific drug delivery for orally administered diclofenac sodium and 5-aminosalicylic acid", "World Journal of Gastroenterology", 2004, pp. 1769-1774, vol. 10, No. 12, Publisher: WJG Press.

Thakral, S., et al., "Eudragit: a technology evaluation", "Expert Opinion on Drug Delivery", 2013, pp. 131-149, DOI:10.1517/17425247.2013.736962, vol. 10, No. 1.

Zahirul, M., et al., "A pH-Dependent Colon-Targeted Oral Drug Delivery System Using Methacrylic Acid Copolymers. II. Manipulation of Drug Release Using Eudragit L100 and Eudragit S100 Combinations", "Drug Development and Industrial Pharmacy", 2000, pp. 549-554, vol. 26, No. 5.

Zhang, S-Q, et al., "In vitro and in vivo evaluation of tegaserod maleate pH-dependent tablets", "European Journal of Pharmaceutics and Biopharmaceutics", 2008, pp. 247-254, vol. 69, Publisher: Elsevier.

\* cited by examiner

FORMULATION HAVING IMPROVED PH-DEPENDENT DRUG-RELEASE CHARACTERISTICS, CONTAINING ESOMEPRAZOLE OR PHARMACEUTICALLY ACCEPTABLE SALT THEREOF

CROSS-REFERENCE TO RELATED APPLICATIONS

This application is a U.S. national phase under the provisions of 35 U.S.C. § 371 of International Patent Application No. PCT/KR17/07933 filed Jul. 24, 2017, which in turn claims priority under 35 U.S.C. § 119 of Korean Patent Application No. 10-2016-0094238 filed Jul. 25, 2016. The disclosures of such International Patent Application No. PCT/KR17/07933 and Korean Patent Application No. 10-2016-0094238 are hereby incorporated herein by reference in their respective entireties, for all purposes.

TECHNICAL FIELD

The present invention relates to a novel formulation having improved pH-dependent drug release characteristics containing esomeprazole or a pharmaceutically acceptable salt thereof, and a method of preparing the same.

BACKGROUND ART

Esomeprazole [(S)-5-methoxy-2-[(4-methoxy-3,5-dimethylpyridin-2-yl)methylsulfinyl]-3H-benzoimidazole)] is a kind of proton pump inhibitor (PPI) having the structure of represented by Formula 2 as an (S)-enantiomer, among two optical isomers of omeprazole having the structure represented by Formula 1. Among the two optical isomers of omeprazole, the (R)-enantiomer is more rapidly metabolized into an inactive metabolite (not an active metabolite) and has a greater difference in metabolic rate between individuals, as compared to the (S)-enantiomer. Thus, the (R)-enantiomer has more side effects, poorer treatment effects and less uniform treatment rates than the (S)-enantiomer, while the (S)-enantiomer, that is, esomeprazole, has an advantage of less effect on liver metabolism, as compared to the (R)-enantiomer as well as omeprazole racemate.

On the other hand, esomeprazole is easily decomposed or transformed under acidic conditions. Thus, oral formulations containing esomeprazole should not contact acidic gastric juice and should be delivered to the site of the gastrointestinal tract where pH is nearly neutral and rapid absorption can occur. For this reason, a formulation using a method such as forming an enteric coated layer has been actively developed.

However, research on esomeprazole formulations has focused to date only on the development of enteric coating for absorption in the intestine, while preventing exposure to stomach acid in the stomach. The development on formulations, which start to be released at a specific time after the target delay time after oral administration, continue to be released for the desired period of time, and finish the release after a specific time, based on studies on pH-dependent release characteristics, was insufficient and unsatisfactory. In this context, there is an urgent and increasing need for new formulations containing esomeprazole with such improved pH-dependent release characteristics and pharmaceutically acceptable salts thereof.

Under these technical backgrounds, the present inventors have found that the pH-dependent release characteristics of esomeprazole or a pharmaceutically acceptable salt thereof can be significantly improved when an endothelial coated layer is formed on a core containing esomeprazole or a pharmaceutically acceptable salt thereof, a release-control coated layer containing a polymer composed of a methacrylic acid copolymer S and a methacrylic acid copolymer L mixed in a specific ratio is present on the endothelial coated layer, and the methacrylic acid copolymer S and the methacrylic acid copolymer L contained in the release-control coated layer are present in a certain ratio, with respect to the weight of an endothelial coated tablet or the endothelial coated layer, thereby completing the present invention.

SUMMARY OF THE INVENTION

Therefore, it is an object of the present invention to provide a novel pharmaceutical formulation having improved pH-dependent drug release characteristics con-

TABLE 1

Structures of omeprazole and esomeprazole

| Structure of Omeprazole | Structure of Esomeprazole |
|---|---|
|  | |

The proton pump inhibitor to which esomeprazole belongs has an advantage of inhibiting secretion of gastric acid in mammals including humans by regulating secretion of gastric acid in the last stage of the acid secretion pathway. Thus, the proton pump inhibitor can be used to prevent and treat gastric and esophageal reflux diseases such as reflux esophagitis, and diseases associated with gastric hyperproliferation including gastritis, duodenitis, gastric ulcer, duodenal ulcer and peptic ulcer.

taining esomeprazole or a pharmaceutically acceptable salt thereof, and a method of preparing the same.

In accordance with the present invention, the above and other objects can be accomplished by the provision of a pharmaceutical formulation including (a) a core containing esomeprazole or a pharmaceutically acceptable salt thereof as an active ingredient, (b) an endothelial coated layer formed on the core, and (c) a release-control coated layer formed on the endothelial coated layer, wherein an endothelial coating material contained in the endothelial coated layer, and a methacrylic acid copolymer S and a methacrylic acid copolymer L contained as release-control coating base materials in the release-control coated layer are present in a certain content ratio.

The pharmaceutical formulation may be selected from the group consisting of a pellet, a mini-tablet (MUST), a tablet, a mixture of a pellet and a mini-tablet, and a capsule, but the present invention is not limited thereto. The pellet and/or the mini-tablet may be incorporated in a capsule.

In accordance with another aspect of the present invention, provided is a method of preparing a pharmaceutical formulation containing esomeprazole or a pharmaceutically acceptable salt thereof, including (a) mixing esomeprazole or a pharmaceutically acceptable salt thereof with a diluent, (b) adding a disintegrant, a binder and a lubricant to the mixture of step (a), followed by mixing, (c) dry-granulating the mixture of step (b) and then tableting to obtain a mini-tablet (MUST) or tablet, (d) endothelially coating the tableted mini-tablet or tablet obtained in step (c) using a fluidized bed dryer (FBG) and a coater, and (e) forming a release-control coated layer using a mixture containing a methacrylic acid copolymer S and a methacrylic acid copolymer L in the endothelially coated mini-tablet or tablet obtained in step (d).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

BEST MODE FOR CARRYING OUT THE INVENTION

Unless defined otherwise, all technical and scientific terms used herein have the same meaning as those appreciated by those skilled in the field to which the present invention pertains. In general, nomenclature used herein is well-known in the art and is ordinarily used.

In one aspect, the present invention provides a pharmaceutical composition containing esomeprazole or a pharmaceutically acceptable salt thereof, including:

(a) a core containing esomeprazole or a pharmaceutically acceptable salt thereof as an active ingredient;

(b) an endothelial coated layer formed on the core; and (c) a release-control coated layer formed on the endothelial coated layer and containing a polymer composed of a methacrylic acid copolymer S and a methacrylic acid copolymer L mixed in a specific ratio, wherein the endothelial coated layer contains at least one selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC), the release-control coated layer contains a mixture of a methacrylic acid copolymer S and a methacrylic acid copolymer L in a ratio of 1.5:1 to 3.5:1 (w/w), preferably 2:1 to 3:1, and the weight of the methacrylic acid copolymer S and the methacrylic acid copolymer L as the release-control coating base materials is 15 to 40% (w/w), preferably 20 to 35% (w/w), with respect to the weight of an endothelial coated tablet.

The pharmaceutical formulation according to the present invention is preferably provided in the form of a pellet, a mini-tablet (MUST), a tablet, a mixture of a pellet and a mini-tablet, or a capsule, but is not limited thereto, and the pellet or mini-tablet provided may be incorporated in a capsule.

The pharmaceutical formulation according to the present invention is almost not degraded in the stomach and starts dissolution of esomeprazole or a pharmaceutically acceptable salt thereof in the gastrointestinal tract in the pH range of 6.5 to 7.0. In particular, the pharmaceutical formulation starts dissolution of the esomeprazole or a pharmaceutically acceptable salt thereof at pH of 6.7 to 6.9 after a delay time of 2 hours and then finishes the dissolution after 6 hours, thus having advantages of obtaining high patient convenience and excellent therapeutic effect.

In the pharmaceutical formulation according to the present invention, any pharmaceutically acceptable salt of esomeprazole can be used without limitation as long as it is ordinarily used in the art, and preferred examples of the pharmaceutically acceptable salt of esomeprazole include, but are not limited to, a metal salt, such as, a magnesium (Mg) salt, a strontium (Sr) salt, a lithium salt, a sodium salt, a potassium salt or a calcium salt of esomeprazole, and an ammonium salt of esomeprazole. Most preferably, a magnesium salt or a strontium salt of esomeprazole is used.

In addition, in the pharmaceutical formulation according to the present invention, the esomeprazole or a pharmaceutically acceptable salt thereof may be used in the form of an anhydride or hydrate thereof.

In the pharmaceutical formulation according to the present invention, the core containing esomeprazole or a pharmaceutically acceptable salt thereof may also contain an appropriate amount of an ordinarily acceptable excipient, in addition to the esomeprazole or a pharmaceutically acceptable salt thereof as an active ingredient. Preferably, the core may contain one or more excipients selected from diluents, binders, disintegrants, lubricants, surfactants, antioxidants, preservatives and stabilizers, but is not limited thereto.

The diluent, which may be contained in the core of the pharmaceutical formulation according to the present invention, may include at least one selected from the group consisting of mannitol, microcrystalline cellulose, lactose, cellulose and derivatives thereof, dibasic or tribasic calcium phosphate, erythritol, low-substituted hydroxypropyl cellulose, pregelatinized starch, sorbitol and xylitol. However, mannitol and/or microcrystalline cellulose are preferably used.

The binder may be selected from the group consisting of hydroxypropyl cellulose (HPC), copovidone (copolymer of vinylpyrrolidone with other vinyl derivatives), hydroxypropyl methyl cellulose (HPMC), polyvinyl pyrrolidone (povidone), pregelatinized starch and low-substituted hydroxypropyl cellulose (HPC-L), but is not limited thereto. Hydroxypropyl cellulose is preferably used.

The disintegrant may include at least one selected from the group consisting of croscarmellose sodium, corn starch, crospovidone, low-substituted hydroxypropyl cellulose (HPC-L) or pregelatinized starch, but is not limited thereto. Preferably, croscarmellose sodium is used.

The lubricant may include at least one selected from the group consisting of sodium stearyl fumarate, magnesium stearate, talc, polyethylene glycol, calcium behenate, calcium stearate and hydrogenated castor oil, but is not limited thereto. Preferably, sodium stearyl fumarate is used.

In the pharmaceutical formulation according to the present invention, the endothelial coated layer formed on the core containing esomeprazole or a pharmaceutically acceptable salt thereof includes at least one substance selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC). Preferably, hydroxypropyl methyl cellulose (HPMC) is used.

As used herein, the term "endothelial coated tablet" means a mini-tablet (MUST) having an endothelial coated layer formed on a core containing esomeprazole or a pharmaceutically acceptable salt thereof as an active ingredient.

The at least one substance selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC), contained in the endothelial coated layer is preferably present in a content ratio of 4.4 to 5.2% (w/w), preferably, 4.7 to 4.9% (w/w), with respect to the weight of the endothelial coated tablet.

In the pharmaceutical formulation according to the present invention, the release-control coated layer formed on the endothelial coated layer (which can be used interchangeably with "enteric coated layer" herein) contains a mixture of a methacrylic acid copolymer S and a methacrylic acid copolymer L as release-control coating base materials at a ratio of 1.5:1 to 3.5:1 (w/w), preferably 2:1 to 3:1 (w/w).

The methacrylic acid copolymer S is an anionic copolymer containing methacrylic acid and methyl methacrylate in a ratio of about 1:2, which is sold under the trade name "Eudragit S-100" and the methacrylic acid copolymer L is an anionic copolymer containing methacrylic acid and methyl methacrylate in a ratio of about 1:1, which is sold under the trade name "Eudragit L-100".

As used herein, the term "release-control coated tablet" means a mini-tablet (MUST) or tablet having a release-control coated layer formed on the endothelial coated layer.

In the pharmaceutical formulation according to the present invention, the release control coating base materials contained in the release-control coated layer, namely, the methacrylic acid copolymer S and the methacrylic acid copolymer L, are present in an amount of 15 to 40% (w/w), preferably 20 to 35% (w/w), with respect to the weight of the endothelial coated tablet.

The content ratio of at least one substance selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC) present in the endothelial coated layer, with respect to the weight of the methacrylic acid copolymer S and the methacrylic acid copolymer L, is 3.5 to 8.0 (w/w), preferably 4.2 to 7.4 (w/w).

In addition, the pharmaceutical formulation according to the present invention is characterized in that, in the release (dissolution) test using an artificial intestinal fluid (medium) having a pH of about 6.7 to 6.9 under the conditions of a number of revolutions of 75 rpm and 37° C. in accordance with the USP paddle method, 5% or less, preferably 2% or less of the esomeprazole or a pharmaceutically acceptable salt thereof is eluted after 2 hours and 90% or more, preferably 98% or more of the esomeprazole or a pharmaceutically acceptable salt thereof is eluted after 6 hours.

When the content ratio of at least one substance selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC) present in the endothelial coated layer, with respect to the weight of the methacrylic acid copolymer S and the methacrylic acid copolymer L, as the release-control coating base material according to the present invention, is less than 3.5 (w/w) or higher than 8.0 (w/w), the esomeprazole or a pharmaceutically acceptable salt thereof begins to be eluted prior to the desired delay time according to the present invention, or the esomeprazole or a pharmaceutically acceptable salt thereof is not eluted sufficiently till a desired dissolution time.

When the amount of at least one substance selected from the group consisting of hydroxypropyl methyl cellulose (HPMC), polyvinyl pyrrolidone (PVP), low-substituted hydroxypropyl cellulose (HPC-L), starch, gelatin and ethyl cellulose (EC), with respect to the weight of the endothelial coated tablet, is less than 4.4 (w/w) or higher than 5.2 (w/w), the esomeprazole or a pharmaceutically acceptable salt thereof begins to be eluted prior to the desired delay time, the or esomeprazole or a pharmaceutically acceptable salt thereof is not eluted sufficiently till a desired dissolution time.

In another aspect, the present invention provides a method of preparing a pharmaceutical formulation containing esomeprazole or a pharmaceutically acceptable salt thereof as an active ingredient.

Specifically, the method of preparing a pharmaceutical formulation containing esomeprazole or a pharmaceutically acceptable salt thereof as an active ingredient will be described as an example in which the formulation is a mini-tablet (MUST) or a tablet. Specifically, the pharmaceutical formulation may be prepared by the process including, but is not limited to:

(a) mixing esomeprazole or a pharmaceutically acceptable salt thereof with a diluent;

(b) adding a disintegrant, a binder and a lubricant to the mixture of step (a), followed by mixing;

(c) dry-granulating the mixture of step (b) and then tableting to obtain a mini-tablet or tablet;

(d) endothelially coating the tableted mini-tablet or tablet obtained in step (c) using a fluidized bed dryer (FBG) and a coater; and (e) forming a release-control coated layer using a mixture containing a methacrylic acid copolymer S and a methacrylic acid copolymer L in the endothelially coated mini-tablet or tablet obtained in step (d).

In another aspect, the present invention provides the use of a pharmaceutical formulation containing esomeprazole or a pharmaceutically acceptable salt thereof as an active ingredient for preventing and treating gastric and esophageal reflux diseases such as reflux esophagitis, and diseases associated with gastric hyperproliferation including gastritis, duodenitis, gastric ulcer, duodenal ulcer and peptic ulcer, and a method for preventing and treating a pharmaceutical formulation containing esomeprazole or a pharmaceutically acceptable salt thereof as an active ingredient for preventing and treating gastric and esophageal reflux diseases such as reflux esophagitis, and diseases associated with gastric hyperproliferation including gastritis, duodenitis, gastric ulcer, duodenal ulcer and peptic ulcer, including administering the pharmaceutical formulation according to the present invention to a patient in need of the treatment.

EXAMPLE

Hereinafter, the present invention will be described in more detail with reference to examples. However, it is obvious to those skilled in the art that these examples are provided only for illustration of the present invention and should not be construed as limiting the scope of the present invention.

Examples 1 to 4

Preparation of Tablets Containing Esomeprazole Magnesium Salt

An esomeprazole magnesium salt and mannitol were mixed and granulated through a 30-mesh round sieve. The resulting mixture was blended with microcrystalline cellulose, croscarmellose sodium, hydroxypropyl cellulose and sodium stearyl fumarate in an empty blender for 15 minutes to prepare a final mixture. The final mixture was dry-granulated in a roller compactor and the obtained granules obtained were granulated through a 20 mesh round sieve.

Then, a mini tablet (MUST) having a hardness of about 1 to 2 kp and a predetermined weight of 7.5 mg was prepared by tabletting using a MUST punch having a diameter of 2.0 mm with a tabletting machine.

The composition of the final core containing an esomeprazole magnesium salt is shown in Table 2.

TABLE 2

Composition of core containing esomeprazole magnesium salt

| | Ingredient | Weight (mg/10 Tablet) | Weight (%) |
|---|---|---|---|
| Core | Esomeprazole magnesium salt | 21.7 | 28.9 |
| | Microcrystalline cellulose | 15.0 | 20.0 |
| | Mannitol | 30.5 | 40.7 |
| | Croscarmellose sodium | 2.4 | 3.2 |
| | Hydroxypropyl cellulose | 2.4 | 3.2 |
| | Sodium stearyl fumarate | 3.0 | 4.0 |
| | Total | 75.0 | 100.0 |

Then, the tablet was coated in accordance with the composition of Table 3 in a fluidized bed coater to obtain an endothelial coated tablet with a weight of 7.88 mg.

The HPMC was present in the endothelial coated tablet at a content ratio of 4.82 (w/w), with respect to the weight of the endothelial coated tablet.

TABLE 3

Composition of endothelial coated tablet

| | Ingredient | Weight (mg/10 Tablet) | Weight (%) |
|---|---|---|---|
| Endothelial coated tablet | Hydroxypropyl methyl cellulose | 3.8 | 100.0 |
| | Purified water | (appropriate amount) | — |
| | Total | 78.8 | 100.0 |

Subsequently, the above-mentioned endothelial coated tablets were coated in accordance with the composition of Table 4 in a fluidized bed coater to prepare coated tablets (release-control coated tablets) having release-control coated layers (enteric coated layers) as shown in Examples 1 to 4.

TABLE 4

Composition of release-control coated layer according to Examples of present invention

| | | Weight (mg/10 Tablet) | | | |
|---|---|---|---|---|---|
| | | Eudragit S/L = 2:1 | | Eudragit S/L = 3:1 | |
| | Ingredient | Example 1 | Example 2 | Example 3 | Example 4 |
| Release-control coated layer | Eudragit S-100 | 13.3 | 18.6 | 12.0 | 18.0 |
| | Eudragit L-100 | 6.7 | 9.4 | 4.0 | 6.0 |
| | Triethyl citrate | 2.0 | 2.8 | 1.6 | 2.4 |
| | Talc | 10.0 | 14.0 | 8.0 | 12.0 |
| | Ethanol | (appropriate amount) | (appropriate amount) | (appropriate amount) | (appropriate amount) |
| | Distilled water | (appropriate amount) | (appropriate amount) | (appropriate amount) | (appropriate amount) |
| | Total | 110.8 | 123.6 | 104.4 | 117.2 |

Examples 1 and 2 in Table 4 relate tables wherein Eudragit S-100 and L-100 as release-control coating base materials are mixed in a ratio of 2:1 and a release-control coated layer is coated in a content ratio of 25 to 35% (w/w), with respect to the weight of an endothelial coated tablet. Examples 3 and 4 relate to tables wherein Eudragit S-100 and L-100 as release-control coating base materials are mixed in a ratio of 3:1 and the release-control coating base material is coated in a content ratio of 20 to 30% (w/w), with respect to the weight of the endothelial coated tablet. In addition, the content ratio of HPMC contained in the endothelial coated layer, with respect to the total weight of the release-control coating base materials, that is, the methacrylic acid copolymer S and the methacrylic acid copolymer L, contained in the release-control coated layer, is 4.21 to 7.37 (w/w).

Overall, Table 5 summarizes content ratios and the like, of respective ingredients in pharmaceutical formulations according to examples of the present invention.

TABLE 5

Compositions and content ratios of pharmaceutical formulation according to examples of present invention

| | Weight (mg/10 Tablet) | | | |
| --- | --- | --- | --- | --- |
| | Eudragit S/L = 2:1 | | Eudragit S/L = 3:1 | |
| Ingredient | Example 1 | Example 2 | Example 3 | Example 4 |
| Weight of release-control coating base material | 20 | 28 | 16 | 24 |
| Weight of HPMC | 3.8 | 3.8 | 3.8 | 3.8 |
| Weight of endothelial coated tablet | 78.8 | 78.8 | 78.8 | 78.8 |
| Weight of release-control coated tablet | 110.8 | 123.6 | 104.4 | 117.2 |
| Weight of release-control coating base material/weight of HPMC | 5.26 | 7.37 | 4.21 | 6.32 |
| Weight of release-control coating base material/weight of endothelial coated tablet | 25.38% | 35.53% | 20.30% | 30.46% |
| Weight of release-control coating base material/weight of release-control coated tablet | 18.05% | 22.65% | 15.33% | 20.48% |
| Weight of HPMC/weight of endothelial coated tablet | 4.82% | 4.82% | 4.82% | 4.82% |
| Weight of HPMC/weight of release-control coated tablet | 3.43% | 3.07% | 3.64% | 3.24% |

Comparative Examples 1 to 6

Preparation of Tablets of Esomeprazole Magnesium Salt

Tablets of Comparative Examples 1 to 6 wherein the mini-tablet endothelially coated in accordance with the production methods of Examples 1 to 4 is provided with the release-control coated layer formed in accordance with the composition of Table 6 were prepared.

Comparative Examples 1 and 2 in Table 6 are compositions wherein Eudragit S-100 and Eudragit L-100 are mixed in a ratio of 2:1 and the release-control coating base material is coated in a content ratio of 10 to 40% (w/w), with respect to the weight of the endothelial coated tablet. In addition, Comparative Examples 3 and 4 relate to tablets wherein Eudragit S-100 and Eudragit L-100 are mixed in a ratio of 3:1 and the release-control coating base material is coated in a content ratio of 10 to 40% (w/w), with respect to the weight of the endothelial coated tablet.

Comparative Examples 5 and 6 relate to tablets wherein Eudragit S-100 and Eudragit L-100 are mixed in a ratio of 6:1 and the release-control coating base material is coated in a content ratio of 10 to 20% (w/w), with respect to the weight of the endothelial coated tablet.

TABLE 6

Composition of release-control coated layer according to Comparative Examples of present invention

| | | Weight (mg/10 Tablet) | | | | | |
| --- | --- | --- | --- | --- | --- | --- | --- |
| | | Eudragit S/L = 2:1 | | Eudragit S/L = 3:1 | | Eudragit S/L = 6:1 | |
| | Ingredient | Example 1 | Example 2 | Example 3 | Example 4 | Example 5 | Example 6 |
| Enteric coating | Eudragit S-100 | 5.3 | 21.2 | 6.0 | 24.0 | 6.86 | 13.7 |
| | Eudragit L-100 | 2.7 | 10.8 | 2.0 | 8.0 | 1.14 | 2.3 |
| | Triethyl citrate | 0.8 | 3.2 | 0.8 | 3.2 | 0.8 | 1.6 |
| | Talc | 4.0 | 16.0 | 4.0 | 16.0 | 4.0 | 8.0 |
| | Ethanol | (appropriate amount) | (appropriate amount) | (appropriate amount) | (appropriate amount) | (appropriate amount) | (appropriate amount) |
| | Distilled water | (appropriate amount) | (appropriate amount) | (appropriate amount) | (appropriate amount) | (appropriate amount) | (appropriate amount) |
| | Total | 91.6 | 130.0 | 91.6 | 130.0 | 91.6 | 104.4 |

Overall, the content ratios and the like of respective ingredients of pharmaceutical formulations according to Comparative Examples of the present invention are summarized in Table 7.

TABLE 7

Compositions and content ratios of pharmaceutical formulations according to comparative examples of present invention

| | Weight (mg/10 Tablet) | | | | | |
|---|---|---|---|---|---|---|
| | Eudragit S/L = 2:1 | | Eudragit S/L = 3:1 | | Eudragit S/L = 6:1 | |
| Ingredient | Comparative Example 1 | Comparative Example 2 | Comparative Example 3 | Comparative Example 4 | Comparative Example 5 | Comparative Example 6 |
| Weight of release-control coating base material | 8 | 32 | 8 | 32 | 8 | 16 |
| Weight of HPMC | 3.8 | 3.8 | 3.8 | 3.8 | 3.8 | 3.8 |
| Weight of endothelial coated tablet | 78.8 | 78.8 | 78.8 | 78.8 | 78.8 | 78.8 |
| Weight of release-control coated tablet | 91.6 | 130 | 91.6 | 130 | 91.6 | 140.4 |
| Weight of release-control coating base material/weight of HPMC | 2.11 | 8.42 | 2.11 | 8.42 | 2.11 | 4.21 |
| Weight of release-control coating base material/weight of endothelial coated tablet | 10.15% | 40.61% | 10.15% | 40.61% | 10.15% | 20.30% |
| Weight of release-control coating base material/weight of release-control coated tablet | 8.73% | 24.62% | 8.73% | 24.62% | 8.73% | 15.33% |
| Weight of HPMC/weight of endothelial coated tablet | 4.82% | 4.82% | 4.82% | 4.82% | 4.82% | 4.82% |
| Weight of HPMC/weight of release-control coating base material | 4.15% | 2.92% | 4.15% | 2.92% | 4.15% | 3.64% |

Test Example 1

The dissolution rates of esomeprazole magnesium salts were measured over time under the conditions shown in Table 8 using the formulations of Examples 1 to 4 and the formulations of Comparative Examples 1 to 6.

TABLE 8

Measurement conditions of dissolution rates of esomeprazole magnesium salts

| Dissolution conditions | |
|---|---|
| Dissolution fluid | Artificial intestinal fluid 900 mL (pH 6.8) |
| Apparatus | USP paddle method, 75 rpm |
| Temperature | 37° C. |
| Dissolution time | Analysis at 30, 60, 90, 120, 180, 240, 300, 360 minutes |

| Analysis conditions | |
|---|---|
| Analysis apparatus | HPLC (Hitachi 5000 series, Japan) |
| Detector | UV spectrophotometer (measurement wavelength: 320 nm) |
| Column | Column having stainless steel tube (with inner diameter of about 4.0 mm and length of about 10 cm), filled with silica gel for liquid chromatography (particle diameter: 5 um) |
| Mobile phase | Sodium phosphate buffer (pH 7.3):acetonitrile:distilled water = 50:35:15 |
| Flow rate | 1.0 mL/min |
| Column temperature | 30° C. |

Figure 1:
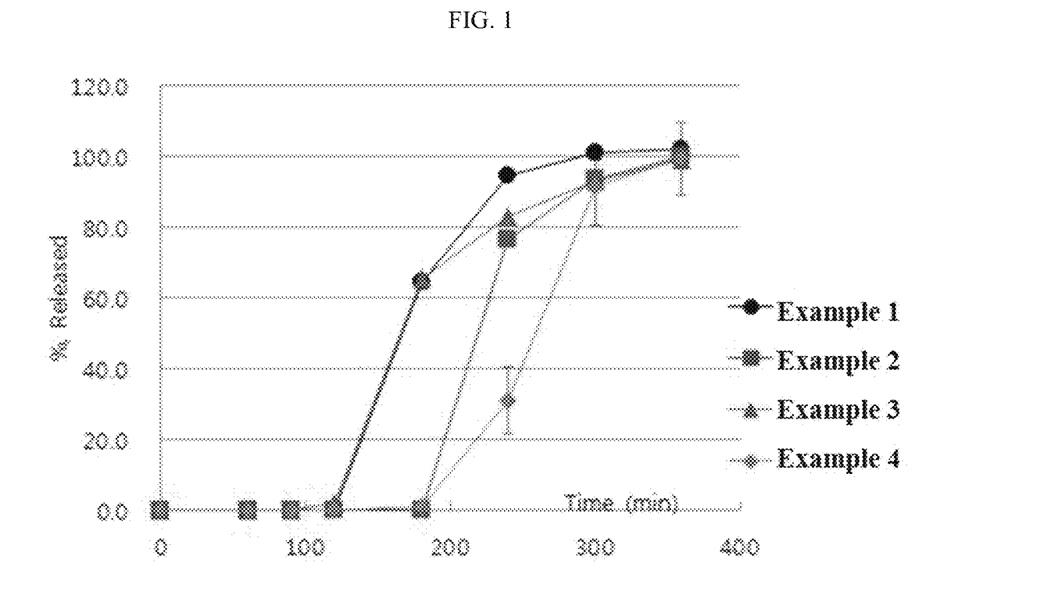
FIG. 1 shows results of a test for release characteristics regarding a pharmaceutical formulation according to the present invention wherein a mix ratio between a methacrylic acid copolymer S and a methacrylic acid copolymer L present as release-control coating base materials in a release-control coated layer is 2:1 to 3:1 (w/w), and the weight of the methacrylic acid copolymer S and the methacrylic acid copolymer L present as the release-control coating base material in the release-control coated layer is 20 to 35% (w/w), with respect to the weight of an endothelial coated tablet.
Figure 2:
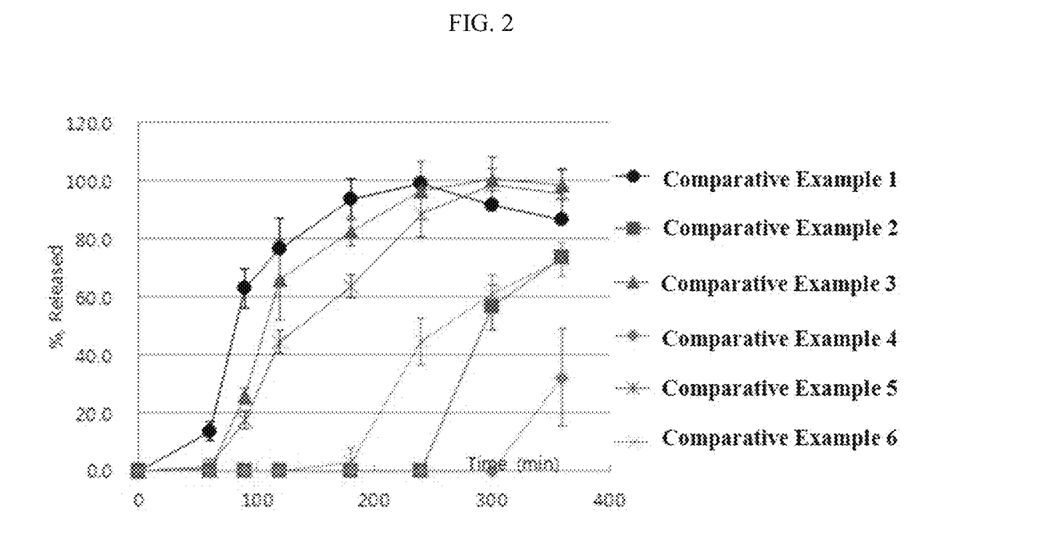
FIG. 2 shows results of a test for release characteristics regarding a comparative pharmaceutical formulation wherein a mix ratio between a methacrylic acid copolymer S and a methacrylic acid copolymer L present as release-control coating base materials in a release-control coated layer is 6:1 (w/w), or the weight of the methacrylic acid copolymer S and the methacrylic acid copolymer L present as the release-control coating base material in the release-control coated layer is 10 to 40% (w/w), with respect to the weight of the endothelial coated tablet.

The results of the measurement of the dissolution rate are shown in Tables 9 and 10 and FIGS. 1 and 2. As can be seen from Table 9 and FIG. 1, in Examples 1 to 4, a drug-release delay of 2 hours or longer in the artificial intestinal fluid is possible and the release is accelerated once the release starts.

That is, it can be seen that, when the release-control coated layer contains a polymer composed of a methacrylic acid copolymer S and a methacrylic acid copolymer L mixed as release-control coating base materials in a ratio of 1.5:1 to 3.5:1 (w/w), preferably 2:1 to 3:1 (w/w), the weight of the release-control coating base material is 15 to 40% (w/w), preferably 20 to 35% (w/w), with respect to the weight of the tablet containing the endothelial coated layer, and the weight ratio of the release-control coating base material and HPMC in the endothelial coated layer is 3.5 to 8.0 (w/w), preferably 4.2 to 7.4 (w/w), and the weight of HPMC in the endothelial coated layer is 4.4 to 5.2% (w/w), preferably 4.7 to 4.9% (w/w), with respect to the weight of the endothelial coated tablet, the esomeprazole magnesium salt is almost not released for 2 hours, starts to be rapidly released after 2 hours, and 99% or higher thereof is released after 6 hours, meaning very excellent release characteristics.

It can be seen from comparison between Example 1 and Example 3 that, as the ratio of Eudragit S-100, which is relatively insoluble in artificial intestinal fluids, increases, sufficient drug release delay is possible in spite of using a relatively small amount of release-control coating base material.

On the other hand, as can be seen from Comparative Example 1 and Comparative Example 3, when the amount of the release-control coated agent used is lower than that of Examples (wherein the release-control coating base material is used at 10% or less, with respect to the endothelial coated core tablet), the effect of drug release delay in artificial intestinal fluids is poor, and as can be seen from Comparative Example 2 and Comparative Example 4, when the amount of the release-control coated agent used is higher than that of Examples (wherein the release-control coating base material is used at 40% or more, with respect to the endothelial coated core tablet), rapid drug release delay is difficult and drug release is not completed even after 6 hours, so that the drug may be excreted before being absorbed in vivo.

In addition, considering Comparative Example 5 and Comparative Example 6 having a high rate of relative insoluble Eudragit S-100 in the artificial intestinal fluid, when the release-control coating base material was used at 10% or less with respect to the endothelial coated core tablet, the effect of release delay was poor, and when the release-control coating base material was used at 20% or more, disadvantageously, the drug was slowly released over a long period of time after the delay of release, and the final dissolution rate was also below 100%.

TABLE 9

Dissolution rates of esomeprazole magnesium salts (Examples)

| | Dissolution rate (%) | | | | | | | |
|---|---|---|---|---|---|---|---|---|
| | Example 1 | | Example 2 | | Example 3 | | Example 4 | |
| Time (min) | Mean | Standard deviation | Mean | Standard deviation | Mean | Standard deviation | Mean | Standard deviation |
| 0 | 0.0 | 0.0 | 0.0 | 0.0 | 0.0 | 0.0 | 0.0 | 0.0 |
| 60 | 0.0 | 0.0 | 0.0 | 0.0 | 0.0 | 0.0 | 0.0 | 0.0 |
| 90 | 0.0 | 0.0 | 0.0 | 0.0 | 0.0 | 0.0 | 0.0 | 0.0 |
| 120 | 0.0 | 0.0 | 0.0 | 0.0 | 1.8 | 3.1 | 0.0 | 0.0 |
| 180 | 64.6 | 2.1 | 0.0 | 0.0 | 65.5 | 2.6 | 0.9 | 1.5 |
| 240 | 94.4 | 0.2 | 76.4 | 7.7 | 83.2 | 6.6 | 31.1 | 9.7 |
| 300 | 101.2 | 2.1 | 93.8 | 2.0 | 93.2 | 9.7 | 91.7 | 11.1 |
| 360 | 102.1 | 1.2 | 100.2 | 1.0 | 99.4 | 7.7 | 99.5 | 10.2 |

TABLE 10

Dissolution rates of esomeprazole magnesium salts (Comparative Examples)

| | Dissolution rate (%) | | | | | | | | | | | |
|---|---|---|---|---|---|---|---|---|---|---|---|---|
| | Comparative Example 1 | | Comparative Example 2 | | Comparative Example 3 | | Comparative Example 4 | | Comparative Example 5 | | Comparative Example 6 | |
| Time (min) | Mean | Standard deviation | Mean | Standard deviation | Mean | Standard deviation | Mean | Standard deviation | Mean | Standard deviation | Mean | Standard deviation |
| 0 | 0.0 | 0.0 | 0.0 | 0.0 | 0.0 | 0.0 | 0.0 | 0.0 | 0.0 | 0.0 | 0.0 | 0.0 |
| 60 | 13.8 | 3.0 | 0.0 | 0.0 | 0.5 | 0.3 | 0.0 | 0.0 | 1.4 | 2.4 | 0.0 | 0.0 |
| 90 | 62.9 | 6.5 | 0.0 | 0.0 | 25.9 | 2.6 | 0.0 | 0.0 | 17.7 | 3.1 | 0.0 | 0.0 |
| 120 | 76.5 | 10.6 | 0.0 | 0.0 | 65.9 | 13.8 | 0.0 | 0.0 | 44.5 | 4.0 | 0.0 | 0.0 |
| 180 | 93.6 | 7.0 | 0.0 | 0.0 | 82.6 | 4.8 | 0.0 | 0.0 | 63.6 | 4.2 | 3.0 | 5.1 |
| 240 | 99.0 | 1.1 | 0.0 | 0.0 | 96.8 | 10.1 | 0.0 | 0.0 | 88.8 | 8.2 | 44.5 | 8.0 |
| 300 | 91.5 | 0.8 | 56.4 | 7.7 | 100.4 | 3.9 | 0.0 | 0.0 | 98.8 | 9.3 | 61.2 | 6.2 |
| 360 | 86.5 | 0.8 | 73.8 | 2.0 | 98.8 | 5.3 | 32.3 | 16.9 | 95.7 | 7.9 | 72.9 | 5.6 |

The present invention has been described, based on preferred embodiments thereof. Those skilled in the art to which the present invention pertains will appropriate that the present invention can be implemented in modified forms without departing from the spirit and scope of the invention.

Therefore, the embodiments disclosed above should be considered in an illustrative rather than a restrictive sense. The scope of the present invention is defined by the appended claims rather than by the foregoing disclosure and all differences that fall into the scope of equivalents thereto should be construed as being incorporated in the present invention.

INDUSTRIAL APPLICABILITY

The present invention relates to a pharmaceutical formulation containing esomeprazole or a pharmaceutically acceptable salt thereof. The pharmaceutical formulation according to the present invention, based on considerably improved pH-dependent drug release characteristics, starts to release the esomeprazole or a pharmaceutically acceptable salt thereof at a target delay time after oral administration, continues the release for a predetermined time, and finishes the release at a predetermined time, thereby providing excellent patient convenience and excellent therapeutic effects, as compared to conventional other formulations.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

What is claimed is:

1. A pharmaceutical formulation comprising:
   (a) a core containing esomeprazole or a pharmaceutically acceptable salt thereof as an active ingredient;
   (b) an endothelial coated layer formed on the core; and
   (c) a release-control coated layer formed on the endothelial coated layer,
   wherein the endothelial coated layer comprises at least one selected from the group consisting of hydroxypropyl methyl cellulose (HPMC), polyvinyl pyrrolidone (PVP), low-substituted hydroxypropyl cellulose (HPC-L), starch and gelatin,
   the release-control coated layer comprises a polymer in which a methacrylic acid copolymer S and a methacrylic acid copolymer L are mixed in a ratio of 1.5:1 to 3.5:1 (w/w) as release-control coating base materials, and
   wherein the weight of the methacrylic acid copolymer S and the methacrylic acid copolymer L, as the release-control coating base material, is 15 to 40% (w/w), with respect to a weight of the pharmaceutical formulation,
   wherein, in a release test using an artificial intestinal fluid having a pH of 6.7 to 6.9, a number of revolutions of 75 rpm and 37° C. in accordance with the USP paddle method, 5% or less of the esomeprazole or a pharmaceutically acceptable salt thereof is eluted at up to 2 hours, and at least 90% of the esomeprazole or a pharmaceutically acceptable salt thereof is eluted after 6 hours.

2. The pharmaceutical formulation of claim 1, wherein a content ratio of at least one substance selected from the group consisting of hydroxypropyl methyl cellulose (HPMC), polyvinyl pyrrolidone (PVP), low-substituted hydroxypropyl cellulose (HPC-L), starch and gelatin present in the endothelial coated layer, with respect to the weight of the methacrylic acid copolymer S and the methacrylic acid copolymer L, as the release-control coating base materials, is 3.5 to 8.0 (w/w), and
   a content of at least one substance selected from the group consisting of hydroxypropyl methyl cellulose (HPMC), polyvinyl pyrrolidone (PVP), low-substituted hydroxypropyl cellulose (HPC-L), starch and gelatin, contained in the endothelial coated layer, is 4.4 to 5.2% (w/w), with respect to the weight of the tablet pharmaceutical formulation.

3. The pharmaceutical formulation of claim 1, wherein the esomeprazole or a pharmaceutically acceptable salt thereof is an esomeprazole magnesium salt or an esomeprazole strontium salt.

4. The pharmaceutical formulation of claim 1, wherein the esomeprazole or a pharmaceutically acceptable salt thereof is an anhydride or hydrate.

5. The pharmaceutical formulation of claim 1, wherein the core containing esomeprazole or a pharmaceutically acceptable salt thereof further comprises at least one excipient selected from diluents, binders, disintegrants, lubricants, surfactants, antioxidants, preservatives and stabilizers.

6. The pharmaceutical formulation of claim 1, wherein the pharmaceutical formulation is selected from the group consisting of a pellet, a mini-tablet, a tablet, a mixture of a pellet and a mini-tablet, and a capsule.

* * * * *